United States Patent [19]
Hikida et al.

[11] Patent Number: 6,063,777
[45] Date of Patent: May 16, 2000

[54] IMINOCHLORINASPARTIC ACID DERIVATIVES

[75] Inventors: Muneo Hikida; Masahiko Mori, both of Saitama; Isao Sakata, Okayama; Susumu Nakajima, Hokkaido; Hiroyuki Takata, Okayama, all of Japan

[73] Assignees: Wyeth Lederle Japan, Ltd.; Photochemical Co., Ltd., both of Japan

[21] Appl. No.: 09/269,557

[22] PCT Filed: Sep. 30, 1997

[86] PCT No.: PCT/JP97/03484

§ 371 Date: Jun. 15, 1999

§ 102(e) Date: Jun. 15, 1999

[87] PCT Pub. No.: WO98/14753

PCT Pub. Date: Apr. 9, 1998

[30] Foreign Application Priority Data

Oct. 1, 1996 [JP] Japan ...................................... 8-278611

[51] Int. Cl.$^7$ ......................... C07D 487/22; A61K 38/41
[52] U.S. Cl. ........................... 514/183; 540/145; 540/474
[58] Field of Search ............................. 514/183; 540/145, 540/474

[56] References Cited

U.S. PATENT DOCUMENTS 5,770,730  6/1998  Pandey et al. ........................... 540/472

FOREIGN PATENT DOCUMENTS

| 62-5986 | 1/1987 | Japan . |
| 5-97857 | 4/1993 | Japan . |
| 7-188023 | 7/1995 | Japan . |
| 9-124652 | 5/1997 | Japan . |

OTHER PUBLICATIONS

Hardegger., Einfuhrung in das Org–Chem Praktikum., 1958., p. 61.

*Primary Examiner*—Richard L. Raymond
*Assistant Examiner*—Pavanaram K Sripada

*Attorney, Agent, or Firm*—Evenson, McKeown, Edwards & Lenahan, P.L.L.C.

[57] ABSTRACT

The present invention provides an iminochlorin aspartic acid derivative represented by the following formula (I):

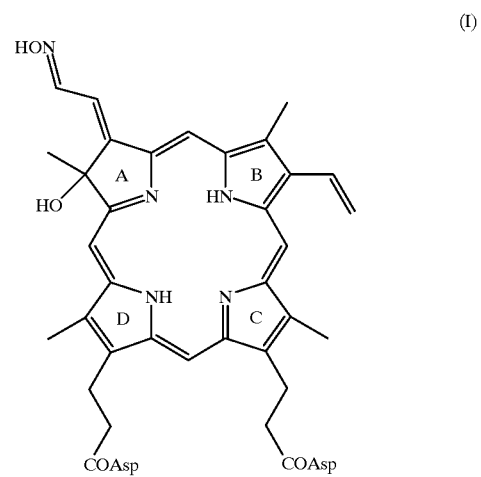

(I)

Wherein Asp represents an aspartic acid residue, or a pharmaceutically acceptable salt thereof. The compound of the present invention is useful as a photosensitizer for photophysico-chemical diagnosis and therapy of cancer, because it has a high accumulability to cancerous cells, reactivity to external energy and a cancerous cell destroying effect which is effective even against cancers developing in deep site, while it is rapidly excreted from normal cells and therefore causes no damage thereto.

9 Claims, 1 Drawing Sheet

IMINOCHLORINASPARTIC ACID DERIVATIVES

This Application is a 371 of PCT/JP97/03484 filed Sep. 30, 1997.

TECHNICAL FIELD

The present invention relates to an iminochlorin aspartic acid derivative or a pharmaceutically acceptable salt thereof. The present invention also relates to a photosensitizer comprising the iminochlorin aspartic acid derivative or a pharmaceutically acceptable salt thereof, which is useful for diagnosis or treatment of human beings or animals.

BACKGROUND ART

As a new method for treatment of cancer, photophysicochemical diagnosis and therapy (PDT: Photodynamic Therapy) has been used. It is a method in which a certain type of porphyrin derivative is administered to a subject by, for example, intravenous injection to retain the porphyrin derivative in the target cancerous tissues in the subject, followed by laser irradiation to cause selective destruction of the cancerous tissues. The therapy utilizes the two properties of a porphyrin derivative, i.e., selectivity for cancerous tissues and photosensitivity.

The only porphyrin derivative currently used in PDT is porphymer sodium. Porphymer sodium is a mixture of products which can be prepared by treating hematoporphyrin with sulfuric acid in acetic acid and then hydrolyzing with 0.1 N sodium hydroxide, and is a 2- to 6-polymer comprising an ether and/or ester of a hematoporphyrin derivative.

However, porphymer sodium is known to cause temporary photosensitivity as an undesirable side effect when administered to man, and further, selective distribution to cancerous tissues is not sufficient for practical use, and therefore the problem of accumulation in normal tissues is present.

Under the circumstances, a patient treated with porphymer sodium is required to stay in the dark for a long period of time until it is completely excreted from the body so that normal cells are not damaged by the photosensitizing action of porphymer sodium accumulated in normal tissues. However, since porphymer sodium shows a slow excretion rate from normal tissues, it sometimes causes photosensitivity to last for more than six weeks.

In addition, PDT using porphymer sodium has a problem with transmission of the light irradiated by laser through tissues. Porphymer sodium has a longest wavelength absorption end at 630 nm and a molar absorption coefficient being as small as 3,000. Since there are many components present in a living body which prevent the transmission of light, such as oxyhemoglobin and water, the light of wavelength of 630 nm exhibits a poor transmission through tissues, which cannot sufficiently reach to deep sites, and therefore, PDT using porphymer sodium is only indicated for cancers developing in the surface layers of 5 to 10 mm depth. The wavelength which is least affected by the light absorption by the components in a living body is in a range of 650 to 750 nm, therefore , photosensitizers for PDT having the longest wavelength absorption end within such range are most desirable.

Laser devices themselves have also a problem. For example, dye lasers which are most commonly used at present have a poor stability in performance and therefore are difficult in handling in practical use. On the other hand, titanium-sapphire lasers enable to facilitate the practice of PDT considerably. However, this type of lasers are limited in the excitable wavelength to not less than 670 nm and not more than 600 nm, and therefore are not applicable to porphymer sodium which has an absorption wavelength of near 630 nm.

Recently, semiconductor lasers (670 nm), which are applicable to compounds exhibiting an absorption near 670 nm, have been developed, and quite recently OPO-YAG laser has been developed, which made it possible to cover almost all of wavelengths.

As mentioned above, photosensitizers currently used for PDT have various defects and therefore development of new agents without such defects is strongly desired. In an attempt to overcome those problems, an agent which is a single compound and exhibits its absorption in a longer wavelength region (650–800 nm) has been proposed as a second generation agent for PDT.

Examples of such second generation agent include aminolevulinic acid (ALA) which is a protoporphyrin precursor; asparthylchlorin e6 (Np e6) which is a chlorin derivative; benzoporphyrin derivative (BPD) and methatetrahydroxyphenylchlorin (m-THPC), both of which are new type of chlorin derivatives obtained by the structural conversion from hemoglobin-derived porphyrins.

In addition, the present inventors proposed chlorin derivatives and the analogues thereof, e.g., a hydroxyiminochlorinyl aspartic acid derivative (NOH-P-Asp) (Japanese Patent Application Laid-open Nos. 5-97857 and 9-124652), confirming that these compounds are useful as photosensitizers for PDT.

However, development of photosensitizers for PDT having more safety and higher therapeutic efficacy is still desired.

Therefore, it is an object of the present invention to provide a photosensitizer suitable for PDT, by finding out a porphyrin derivative which is a single component, is stable, has a higher excretion rate from normal tissues and thereby has a reduced phototoxicity, while retaining a good accumulability to cancerous tissues and, furthermore, allows the use of a titanium-sapphire laser (wavelength of not less than 670 nm and not more than 600 nm) and a semiconductor laser (wavelength of 670 nm).

The present inventors previously disclosed that when a hydroxyimino group and a residue of aspartic acid are bonded to the side chains of a chlorin, one of porphyrin derivatives, which was derivatively synthesized from hemoglobin-derived protoporphyrin dimethyl ester, a mixture of two types of position isomers represented by the following formulae (I) and (II) was obtained (Japanese Patent Application Laid-open No. 5-97857):

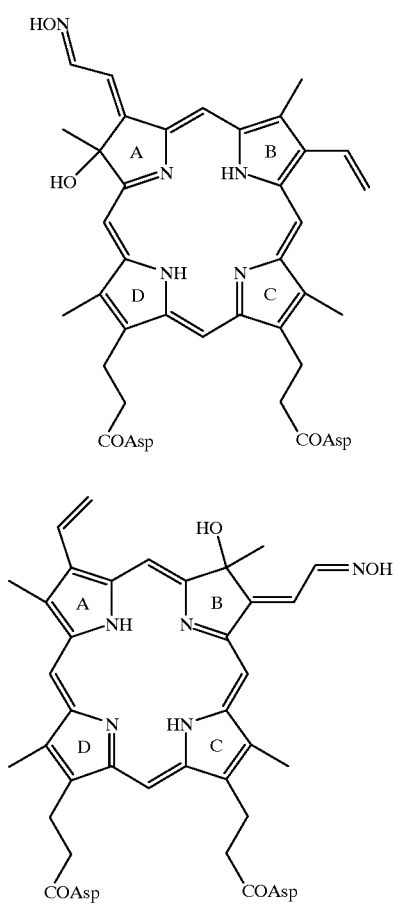

(I)

(II)

wherein Asp represents a residue of aspartic acid.

The present inventors separated these two types of the position isomers from each other by means of chromatographies or recrystallization, and as a result, found that the compound of formula (I) having an imino group in the A-ring thereof has a remarkably superior accumulability to cancerous tissues as compared with the compound of formula (II) having an imino group on the B-ring thereof. In addition, it was also found that the compound of formula (I) also has a strong cell destructing effect induced by a photosensitizing reaction and a quick excretion property from normal tissues, as well as a longest wavelength absorption end at 670 nm or more.

When compound (I) was examined by albumin test [that is, a convenient test method for evaluating the affinity to cancerous tissues, in which a chlorin derivative is examined on the change in ultraviolet (UV) absorption spectrum in a mixture form with albumin and in which one of the present inventors has found a certain rule] and dancyl methionine test [that is, a convenient test method for evaluating the strength of the photoreactivity by thin layer chromatography (TLC) or high performance liquid chromatography (HPLC)] (see Japanese Patent Application Laid-open No. 5-97857), it was confirmed that the compound of formula (I) shows an excellent transferability to cancerous tissues and a strong photosensitivity.

DISCLOSURE OF INVENTION

The present invention has been completed based on the above findings, and an aspect of the present invention provides an iminochlorin aspartic acid derivative represented by the following formula (I):

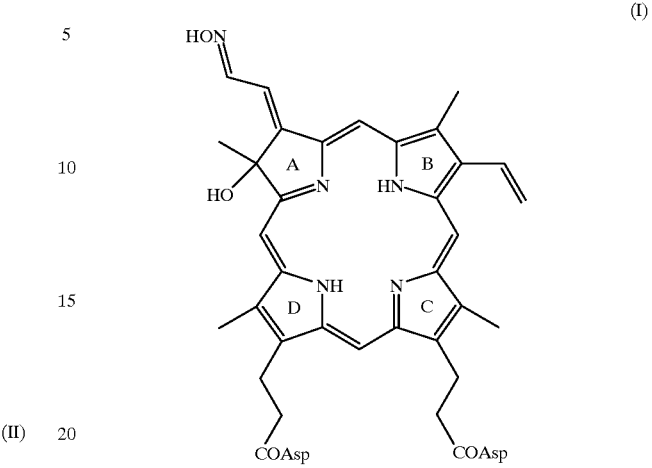

(I)

wherein Asp represents a residue of aspartic acid, or a pharmaceutically acceptable salt thereof.

Another aspect of the present invention provides a photosensitizer for the diagnosis or treatment containing the iminochlorin aspartic acid derivative represented by formula (I) or a pharmaceutically acceptable salt thereof.

A preferable mode of the present invention is a photosensitizer containing the iminochlorin aspartic acid derivative represented by formula (I) or a pharmaceutically acceptable salt thereof to be used for diagnosis or treatment of cancers.

Another preferable mode of the present invention is a photosensitizer containing the iminochlorin aspartic acid derivative represented by formula (I) or a pharmaceutically acceptable salt thereof to be used for diagnosis or treatment of neovascularization in the ophthalmic field.

These photosensitizers are to be used for diagnosis or treatment of man or animals.

BEST MODE FOR CARRYING OUT THE INVENTION

Figure 1:
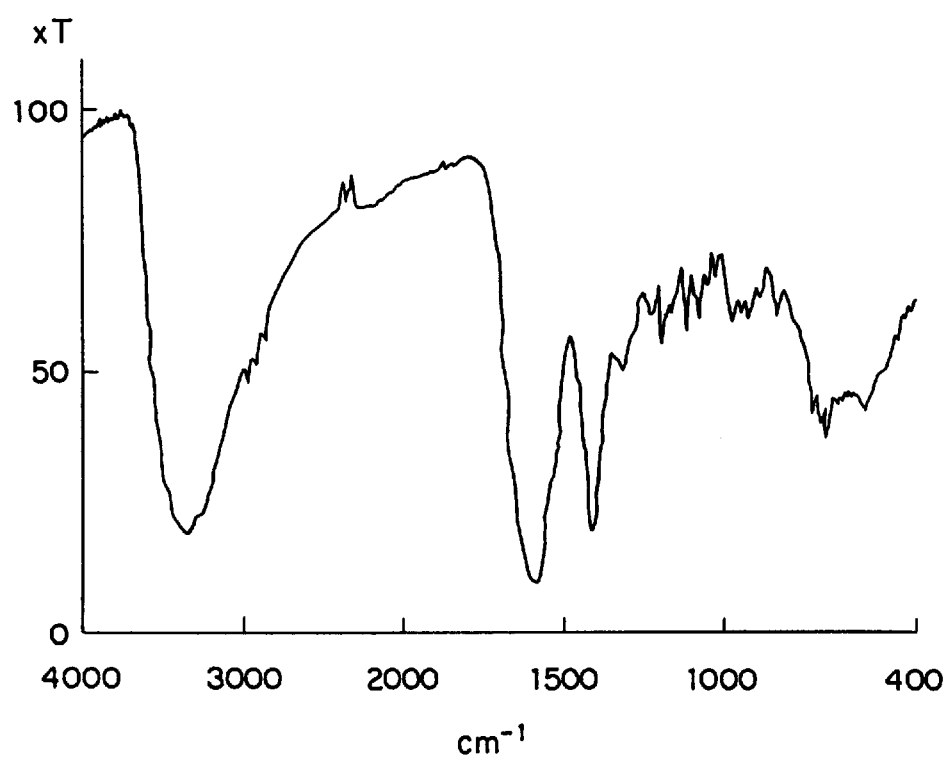
FIG. 1 shows an infrared absorption spectrum of sodium salt of the iminochlorin aspartic acid derivative of formula (I) (NOH-P-Asp).

The iminochlorin aspartic acid derivative represented by formula (I) of the present invention can be prepared by the method as mentioned below.

That is, the compound can be prepared by a method comprising Step (a) in which a protoporphyrin dimethyl ester is converted into a chlorin derivative having an aldehyde group therein; Step (b) in which the aldehyde group of the chlorin derivative thus obtained is bonded with a hydroxyl amine; and Step (c) in which the compound thus obtained is further bonded with aspartic acid via an amide bond. It is not essential to sequentially conduct the reactions in the order of (a), (b) and (c). The order may be varied such as the order of (a), (c) and (b).

The above-mentioned Step (a) gives a mixture of two types of position isomers, i.e., one having an aldehyde group in the A-ring and the other in the B-ring. By isolating and purifying these isomers, the objective chlorin ring derivative having an aldehyde group in the A-ring is obtained, then, by conducting Step (b) and Step (c), the iminochlorin aspartic acid derivative of formula (I) of the present invention can be obtained as a single compound. Alternatively, the isolation and purification of the mixture of the two types of position isomers obtained in Step (a) may be carried out after Step (b) or Step (c) to obtain the compound of formula (I) as a single compound.

Each of the steps is explained in more detail in the following.

Step (a) for conversion of the starting compound into a chlorin derivative can be conducted according to any of the conventional methods, such as methods disclosed in J. E. Falk: "Porphyrins and Metalloporphyrins" published by Elsevier in 1975; D. Dolphin: "The Porphyrins" published by Academic Press in 1978 and so on.

That is, in step (a), protoporphyrin dimethyl ester (hereinafter referred to as "PP-Me") as a starting compound is subjected to a photochemical reaction treatment to give 2-formylethylidene-1-hydroxy-4 -vinyl-deuteroporphyrin dimethyl ester (hereinafter referred to as "P-Me (I)") which is a precursor of the compound of formula (I) of the present invention and 4-formylethylidene-3-hydroxy-2-vinyl-deuteroporphyrin dimethyl ester (hereinafter referred to as "P-Me (II)") which is a position isomer of P-Me (I), in a mixture form. From the mixture thus obtained, each of P-Me (I) and P-Me (II) was isolated and purified by means of silica gel column chromatography or recrystallization using a suitable solvent.

The structure of P-Me (I) obtained above can be determined based on the results of an NOE test as follows.

(1) When 9α-position hydrogen (δ9.79) was irradiated, in the resultant spectrum, NOE was observed at a 7-position hydrogen (δ8.63) and a 3-position methyl hydrogen (δ3.51).
(2) When 9β-position hydrogen (δ10.18). was irradiated, in the resultant spectrum, NOE was observed at a 6-position methylene hydrogen (δ6.43) and an 8-position hydrogen (δ8.39).
(3) When 9δ-position hydrogen (δ9.70) was irradiated, in the resultant spectrum, NOE was observed at a 1-position methyl hydrogen (δ2.56) and a 2-position methylene hydrogen.
(4) When 9γ-position hydrogen (δ10.20) was irradiated, in the resultant spectrum, NOE was observed at a 2-position methylene hydrogen (δ3.33–3.38) and a 5-position methylene hydrogen (δ4.34–4.43).
(5) When each 6-position methylene hydrogen (δ6.43 and 6.17) was irradiated, in the resultant spectrum, NOE was observed at the other 6-position methylene hydrogen (δ6.17 and 6.43).
(6) When 1-position methyl hydrogen (δ2.56) was irradiated, in the resultant spectrum, NOE was observed at a 9δ-position hydrogen and a 10-position hydrogen (δ10.25).

Next, the chlorin compound obtained in Step (a), P-Me (I), is subjected to Step (b). P-Me(I)is reacted with hydroxylamine to obtain 2-hydroxyimino-ethylidene-1-hydroxy-4-vinyl-deuteroporphyrin dimethyl ester (hereinafter referred to as "NOH-P-Me (I)").

This reaction can be conducted according to a conventional procedure as disclosed in "Condensation reaction between hydroxylamine and an aldehyde compound" in Ippan Yuki Kagaku Jikken Sho (Text for General Organic Chemical Experiments).

The thus obtained NOH-P-Me (I) is subjected to Step (c). That is, NOH-P-Me (I) is hydrolyzed with an alkali in a conventional manner and then aminated with aspartic acid methyl ester to obtain 2-hydroxyiminoethylidene-1-hydroxy-4-vinyl-deuteroporphynyl diaspartic acid methyl-ester (hereinafter referred to as "NOH-P-Asp (OMe) (I)").

This reaction may be conducted by a conventional procedure as disclosed in Izumiya et al.,: "*Peptide gosei no kiso to jikken* (Basis and Experiments of Peptide Synthesis)", published by Maruzen in 1985, and especially a procedure as disclosed in Japanese Patent Application Laid-open No. 64-61481, 2-138280, 4-59779, 5-97857 or 9-124652, or Japanese Patent Publication No. 7-25763 are preferred.

The thus obtained methylester of the compound of formula (I) of the present invention may be dissolved in ethanol and then hydrolyzed with sodium hydroxide, thereby giving a sodium salt of the compound of formula (I). The sodium salt may be treated with a suitable weak acid to obtain a free carboxylic acid.

The process for isolation and purification of P-Me (I), a precursor of the compound of formula (I) of the present invention, will be described more concretely in the following by showing representative examples.

When the isolation and purification of P-Me (I) from the mixture of P-Me (I) and P-Me (II) is conducted by means of a silica gel column chromatography, a suitable solvent, e.g., a mixed solvent of hexane/ chloroform may be used. In this process, unreacted PP-Me, P-Me (II), and P-Me (I) are eluted in this order, and therefore the objective P-Me (I) may be obtained by concentrating its fraction, which is the last elution fraction.

On the other hand, when the isolation and purification is conducted by means of recrystallization, it is to be repeated several times using a suitable solvent such as a mixed solvent of tetrahydrofuran/hexane. In this process, unreacted PP-Me, P-Me (II), and P-Me (I) are eluted in this order, and therefore the fraction of P-Me (I), which is the last elution fraction, is to be collected.

It is not essential to conduct the above mentioned chromatography or recrystallization after Step (a), and it may be conducted after Step (b) or (c).

The P-Me (I) thus obtained was subjected to reactions of Steps (b) and (c) as mentioned above, and the resulting compound was hydrolyzed to give the iminochlorin aspartic acid derivative represented by formula (I) (NOH-P-Asp (I)), of the present invention.

On the other hand, P-Me (II), which is a by-product formed when isolating and purifying P-Me (I), was also subjected to Steps (b) and (c) in the same manner as above and the resulting compound was hydrolyzed to give a position isomer of the compound of formula (I) of the present invention, i.e., NOH-P-Asp (II) represented by formula (II). This compound was used as a control in the experiments mentioned later in Examples.

A pharmaceutical preparation comprising the iminochlorin aspartic acid derivative of formula (I) of the present invention can be prepared by per se conventional procedures. For example, the compound may simply be dissolved in a suitable buffer when it is in the form of a free acid, whereas it may simply be dissolved in a physiological saline when it is in the form of a sodium salt. In either case, suitable pharmaceutically acceptable additives may be used, such as a solubilizing agent (e.g., an organic solvent), a pH adjusting agent (e.g., an acid, a base, a buffer), a stabilizer (e.g., ascorbic acid), a vehicle (e.g., maltose) and an isotonicity (e.g., sodium chloride).

The compound of formula (I) of the present invention has satisfactory properties as a photosensitizer for PDT, such as a long phosphorescence life time, a good affinity to albumin, a specific accumulability to a particular organ, especially to a cancer locus and a good cell killing effect when exposed to light as determined by a dancyl methionine test, as well as a satisfactory absorption wavelength, water solubility and purity. The good water solubility of this compound enables preparation of a high concentration solution (e.g., 50 mg/ml). Furthermore, the compound exhibits a high stability in vivo, as well as in vitro. In general, for use as a photosensitizer for PDT, it is desirable to administer the compound to a subject in a dose of 1–5 mg/kg body weight.

As discussed above, the compound of formula (I) of the present invention is structurally characterized in that it has a hydroxyimino group in the A-ring and an aspartic acid residue at the propionic acid side chain of the chlorin skeleton thereof and, as a result, it exhibits various physiological and pharmacological properties.

As one of the properties, the compound selectively accumulates in tumor cells and is excreted therefrom at a slow rate. On the other hand, excretion from normal organs and cells is rapid and therefore it does not damage such organs and cells and does not cause phototoxicity.

Furthermore, according to the present invention, the conversion of a porphyrin into a chlorin derivative allows the absorption wavelength to shift to infrared region and, as a result, it becomes possible to attain therapeutic efficacy for cancers in deep site. Accordingly, the porphyrin derivative of the present invention is highly useful as a photosensitizer for PDT for cancers, malignant tumors, aging macular degeneration associated with choroidal neovascularization and diabetic retinopathy associated with retinal neovascularization in the ophthalmic field.

The present invention will be described in more detail by referring to the following examples.

EXAMPLE 1

Synthesis of photoprotoporphyrin dimethyl ester (P-Me (a mixture of A- and B-ring position isomers)) The title compound was synthesized by the method of P. K. Dinello et al., (see "The Porphyrins", Academic Press, Vol. 1, 303 (1978)) as follows. Protoporphyrin dimethyl ester (PP-Me; 100 g) was dissolved in chloroform (10 L). The resultant reaction mixture was allowed to react with each other for one week under irradiation with light, thereby obtaining a chlorin derivative of the porphyrin. After completion of the reaction, the reaction solution was concentrated under reduced pressure to obtain the title compound (P-Me; 100 g) as a residue.

EXAMPLE 2

Isolation and Purification of the A-ring Position Isomer of P-Me (P-Me (I)) and the B-ring position Isomer of P-Me (P-Me (II)) by Silica Gel Column Chromatography P-Me (100 g) obtained in Example 1 (i.e., a mixture of P-Me (I) and P-Me (II)) was subjected to silica gel chromatography and eluted by a 10% stepwise method (eluent: n-hexane/chloroform) as follows. At first, unreacted PP-Me was eluted out with 50% chloroform solution, then, P-Me (II) (B-ring position isomer; a precursor of the compound (II)) was eluted out with 80% chloroform solution, and at last, P-Me (I) (A-ring position isomer; a precursor of the compound (I) of the present invention) was eluted out with 90% chloroform solution. Each of the resultant solutions was separately concentrated under reduced pressure, thereby obtaining unreacted PP-Me (23.3 g; 23.3%), P-Me (II) (20.0 g; 18.2%) and P-Me (I) (10.0 g; 9.1%), respectively.

EXAMPLE 3

Isolation and Purification of the A-ring Position Isomer (P-Me (I)) and the B-ring position isomer (P-Me (II)) by recrystallization P-Me (100 g) obtained in Example 1 was dissolved in pyridine (1 L), crystallized at 10° C. and filtrated to collect unreacted PP-Me (20.6 g (20.6%)). The resultant filtrate was concentrated under reduced pressure to $2/3$ of its original volume, crystallized again at −10° C. and subjected to filtration, whereby additional unreacted PP-Me (10.5 g (10.5%)) was collected. The resultant filtrate was concentrated under reduced pressure and dissolved in tetrahydrofuran. To the solution was added n-hexane, and the resultant solution was recrystallized at room temperature. The resultant was subjected to filtration to thereby obtain P-Me (II) (8.9 g (8.1%)). Thereafter, the filtrate was concentrated under reduced pressure and then subjected to recrystallization with tetrahydrofuran repeatedly, whereby P-Me (I), which is a precursor of compound (I) of the present invention, was obtained (4.5 g (4.1%)).

$^1$H NMR: δ1.7(3H, s, $\underline{CH_3}$—C—OH), 7.0(1H, d, = $\underline{CH}$—CHO), 11.0 (1H, d, =CH—$\underline{CHO}$);

MS: M$^+$ 622

EXAMPLE 4

Hydroxyimination and Hydrolysis of P-Me (I) and P-Me (II)

Each of P-Me (I) and P-Me (II) obtained in Example 3 was separately weighed out (10 g each) and dissolved in pyridine (190 ml) respectively. To the resultant solution was added a solution of hydroxylamine hydrochloride in pyridine (2 g/20 ml) and allowed to react at room temperature for 1.5 hrs under stirring. After the reaction was completed, the reaction solution was poured into ice water to precipitate a crystalline substance. The crystalline substance was collected by filtration. In this manner, a precursor of the compound (I) of the present invention, hydroxyimino-P-Me (NOH-P-Me (I); 10 g (98%)) was obtained from P-Me (I), and its position isomer, NOH-P-Me (II) (10 g (98%)) was obtained from P-Me (II).

$^1$H NMR: δ2.5 (3H, s, $\underline{CH_3}$—C—OH), 8.6 (1H, d, = $\underline{CH}$—CH=NOH), 10.2 (1H, d, =CH—CH=NOH);

MS: M$^{30}$ : 637

The whole of each of NOH-P-Me (I) and NOH-P-Me (II) obtained in t he above procedure was dissolved in tetrahydrofuran (200 ml) separately. The resultant solution was hydrolyzed with 1N sodium hydroxide solution in a conventional manner and then 20% citric acid solution was added for neutralization, thereby giving a precipitate. The precipitate thus obtained was collected by filtration and dried. In this manner, a precursor of the compound (I) of the present invention, hydroxyimino-P (NOH-P (I); 9.1 g (95%)) was obtained from NOH-P-Me (I), and its position isomer, NOH-P (II) (9.1 g (95%)) was obtained from NOH-P-Me (II).

MS: M$^+$ 609

EXAMPLE 5

Conversion of NOH-P (I) and NOH-P (II) into Aspartic Acid Derivatives Thereof

Each of NOH-P (I) and NOH-P (II) obtained in Example 4 was separately weighed out (2 g each), dissolved in dimethylformamide, and converted into a dicyclohexylamine (DCHA) salt (2.0 g each) with DCHA in a conventional manner, respectively. Each of the resultant DCHA salts was dissolved in dimethylformamide (100 ml). To the resultant solution was added aspartic acid dimethyl ester (AspOMe) hydrochloride (2 g) and further added water soluble carbodiimide (WSC; 2 g) slowly under stirring. Each of the resultant solutions was allowed to react for 10 hrs. After the reaction was completed (The reaction end point was confirmed by TLC.), water was added to each reaction solution to thereby cause precipitation. Each resultant precipitate was washed with water, dried, and recrystallized with acetone/ethyl acetate repeatedly. In this manner, a methyl ester of compound (I) of the present invention, i.e., hydroxyiminoethylidenechlorinyl diaspartic acid methyl ester (NOH-P-Asp(OMe) (I); 0.4 g (13.8%)) was obtained from NOH-P (I), and its position isomer, NOH-P-Asp(OMe) (II)(0.5 g (17.2%)) was obtained from NOH-P (II), as dark greenish brown crystals.

$^1$H NMR: δ2.5(3H, s, CH$_3$—C—OH), 5.2 (1H, m,—CONH—CH—CH$_2$COOCH$_3$), 8.6 (1H, d, =CH—CH—=NOH), 10.2 (1H, d, =CH—CH=NOH);

MS: M$^+$ 895

EXAMPLE 6

Hydrolysis of NOH-P-Asp (OMe) (I and II) (Preparation of sodium salts)

Each of NOH-P-Asp (OMe) (I) and NOH-P-Asp (OMe) (II) obtained in Example 5 was separately weighed out (1 g each) and hydrolyzed in a conventional manner by slowly adding ethyl alcohol (20 ml) and 1N sodium hydroxide (30 ml). After the reaction was completed (The reaction end point was confirmed by TLC.), ethyl alcohol was added to each reaction solution to thereby cause precipitation. Each resultant precipitate was collected by filtration and dissolved in water. To the resultant solution was added ethyl alcohol additionally to thereby cause precipitation. Each resultant precipitate was collected by filtration. This procedure was repeated several times for purification. In this manner, a sodium salt of NOH-P-Asp (I) (compound (I) of the present invention; 0.9 g (87.4%)) was obtained from NOH-P-Asp (OMe) (I), and its position isomer, NOH-P-Asp (II) (a sodium salt of NOH-P-Asp (II); 0.98 g (95.1%)) was obtained from NOH-P-Asp (OMe) (II).

MS: M$^+$ 927

The infrared absorption spectrum of the sodium salt of NOH-P-Asp (I) is shown in FIG. 1.

EXAMPLE 7

Hydrolysis of NOH-P-Asp (OMe) (I and II) (Preparation of free acids)

Each of NOH-P-Asp (OMe) (I) and NOH-P-Asp (II) obtained in Example 5 was separately weighed out (1 g each) and treated in the same manner as in Example 6 for hydrolysis, respectively. To each of the resultant solutions was added twice by volume of water. The mixed solution was neutralized with 5% citric acid solution to cause precipitation. Each resultant precipitate was collected by filtration, washed with water and dried. In this manner, NOH-P-Asp (I) (compound (I) of the present invention; 0.8 g (85.0%)) was obtained from NOH-P-Asp (OMe) (I), and its position isomer, NOH-P-Asp (II) (0.9 g (95.4%)) was obtained from NOH-P-Asp (OMe) (II).

MS: M$^+$ 839

EXAMPLE 8

Laser Irradiation to Extirpated Organ (excited fluorescent spectrum of the surface of the organ)

CDF$_1$ mice (5 per group) were implanted with tumor tissues of colon cancer Colon 26. Two weeks after the implantation, the mice were given an intravenous injection of sodium salt of each of compounds (I) and (II) (10 mg/kg for each mouse) which had been diluted with a distilled water for injection. At 3 hrs, 6 hrs and 12 hrs after the injection, the blood samples were collected and the organs bearing the tumor tissue were extirpated, irradiated with N$_2$-pulsed laser (N$_2$, wavelength: 337 nm, 2 ns), and the excited fluorescent spectrum was measured. The wavelengths in the range of 600 to 900 nm were examined based on the peak wavelength of NADH at 470 nm (determination of the distribution of the test compound in the organ by the surface fluorescence method using N$_2$-pulsed laser spectrophotometry). That is, cancer/organ (or plasma) ratio was determined by calculating the peak wavelength in the range of 600 to 900 nm when the peak wavelength at 470 nm was considered as the basic value, 1. The results are shown in Tables 1 and 2 below.

Table 1 shows the values obtained after administration of the sodium salt of compound (I), and Table 2 shows the values obtained after

TABLE 1

Distribution of Compound (I) in the Body

| Time (hr) | Cancer/Lung | Cancer/Muscle | Cancer/Brain | Cancer/Liver | Cancer/Kidney | Cancer/Plasma |
|---|---|---|---|---|---|---|
| 3 | 5.02 | 4.19 | 11.24 | 1.35 | 1.54 | 1.48 |
| 6 | 7.85 | 3.72 | 15.14 | 2.02 | 1.36 | 1.18 |
| 12 | 6.45 | 4.73 | 15.0 | 0.92 | 1.27 | 2.37 |

TABLE 2

Distribution of Compound (II) in the Body

| Time (hr) | Cancer/Lung | Cancer/Muscle | Cancer/Brain | Cancer/Liver | Cancer/Kidney | Cancer/Plasma |
|---|---|---|---|---|---|---|
| 3 | 2.35 | 1.23 | 10.10 | 0.62 | 0.67 | 0.30 |
| 6 | 4.59 | 1.26 | 16.0 | 1.01 | 0.59 | 1.12 |
| 12 | 2.68 | 2.95 | 15.0 | 1.11 | 0.95 | 0.66 |

As shown in the above tables, compound (I) of the present invention was found to have much higher accumulability to cancerous tissues as compared with its position isomer.

EXAMPLE 9

HeLa cells were seeded in wells of a 96-well plate each containing 100 μl of a culture medium at 5×10$^3$/well, and incubated at 37° C. overnight. In each well, the culture medium was removed, and 100 μl of a solution containing sodium salt of either of compound (I) or compound (II) in concentrations of 0, 6.25, 12.5, 25, 50 and 100 μM/ml was added (3 wells for each group of the concentrations) and incubated at 37° C. at for 6 hrs. Each well was washed with PBS(−) once, and then 100 μl of a fresh medium was added. The wells were irradiated using a diode laser (670 nm) under the conditions of 0.44W of laser intensity, 0.785 cm$^2$ of irradiation area (diameter: 1 cm) and 25 J/cm$^2$ of laser energy. After the irradiation, each well was incubated at 37° C. overnight and washed with PBS(−) once, then 100 μl of a fresh medium was added. To each well was added 20 μl of MTS-PMS reagent, and the well was further incubated at 37° C. for 2–4 hrs. The absorbance of each well at 492 nm was measured using a microplate reader. The cell survival rate at each of the above mentioned concentrations of the test compound was calculated considering the value for the well of 0 μM/ml of the test compound as 100%.

The results are shown in Table 3.

TABLE 3

| | Cell Survival Rate (%) | | | | |
|---|---|---|---|---|---|
| | Concentration ($\mu$M) | | | | |
| | 6.25 | 12.5 | 25 | 50 | 100 |
| Compound (I) | 43 | 19 | 13 | 10 | 10 |
| Compound (II) (Position isomer) | 81 | 54 | 48 | 35 | 19 |

As shown in Table 3, it was confirmed that the compound of formula (I) of the present invention exhibited a remarkably higher cell killing effect against tumor cells compared with the position isomer thereof.

EXAMPLE 10
Study on Occlusion of Choroidal Neoplastic Vessels

The following experiments were performed to investigate the optimal treatment parameters (timing of laser irradiation after dosing of the compound; laser irradiation dosage) for selective occlusion of choroidal neoplastic vessels by PDT using the compound of the present invention and a diode laser (produced by Hamamatsu Photonics; wavelength: 672 nm).

1. Methods

Photocoagulation was induced in rats (Long Evance Rats weighing 200–300 g) by Argon green laser irradiation (irradiation diameter: 100 $\mu$m, 140 mW, 0.1 sec) near the retinal papilla on funduc oculi. Ten days after photocoagulation, fundus photographs and fluorescein angiographs were taken and the animals showing development of choroidal neovascularization were used for experiments at the 11th day.

The compound of the present invention was administered via the tail vein at a dose of 16 mg/kg. After administration, time course distribution of the compound in the eyeball tissues was observed by fluorescence microscopy.

Laser irradiation was done by using the above-mentioned diode laser. The laser beam was confirmed to extend in the range of 500 $\mu$m in diameter on the retinal surface. Duration of irradiation was 4 minutes and the irradiation intensity varied at 30.6, 91.7, 152.9 and 244.9 mW/cm$^2$ on the retinal surface. These values correspond to 7.4, 22.0, 36.7 and 58.8 J/cm$^2$, respectively.

Assessment of the PDT using the compound of the present invention was made based on the fundus photographs taken with a fundus camera (produced by Jenesis Kowa) at 1 hour and 24 hours after laser irradiation. Occlusion of the neoplastic vessels and damage to the surrounding tissues were investigated by fluorescein antiography and histological examinations to assess the selectivity of the therapeutic effect.

2. Results (1) Time course distribution of the compound of the present invention 1) In the preliminary experiments in rats and rabbits, the half-life of the compound of the present invention in blood was 30 minutes after intravenous administration, and the compound was undetectable in blood after 24 hours.
2) Five minutes after administration of the compound of the present invention, weak fluorescence resulting from the compound was observed in the entire choroidal neovascular tissues. However, intensity of the fluorescence did not clearly differ between the neoplastic vessels and the surrounding tissues. In the choroid, fluorescence was observed in the lumens of the choriocapillaris, choroidal arteries and veins. Fluorescence resulting from the compound of the present invention was also observed in the choroidal artery wall. In the retina, prominent fluorescence was observed in the artery wall and weak fluorescence was observed in the lumens of the blood capillaries.
3) From 30 minutes to 1 hour after administration, fluorescence from the whole neoplastic vessels increased.
4) Two hours after administration, prominent fluorescence was observed in the choroidal artery wall, while the fluorescence in the lumens of large choroidal vessels and retinal artery wall diminished. The fluorescence in the choriocapillaris veins disappeared.
5) Four hours after administration, fluorescence in the choroidal artery wall and retinal vessels gradually diminished, while the fluorescence in the choroidal neoplastic vessels persisted.
6) Twenty-four hours after administration, fluorescence in the choroidal neoplastic vessels and other vessels all disappeared.

(2) Effects of laser irradiation Histological findings 24 hours after laser irradiation are shown in Table 4 below.

TABLE 4

| Laser irradiation dosage J/cm$^2$ | Site | Interval between administration of the compound and laser irradiation | | | |
|---|---|---|---|---|---|
| | | Immediately | 60 min | 120 min | 240 min |
| 7.4 | Retinal capillaries | Partially closed | Closed | Open | Open |
| | Choroidal neoplastic vessels | Closed | Closed | Partially closed | Partially Closed |
| | Choriocapillaris | Closed | Closed | Open | Open |
| | Choroidal arteries and veins | Partially closed | Closed | Open | Open |
| 22.0 | Retinal capillaries | Closed | Closed | Open | Open |
| | Choroidal neoplastic vessels | Closed | Closed | Closed | Closed |
| | Choriocapillaris | Closed | Closed | Closed | Closed |
| | Choroidal arteries and veins | Partially closed | Closed | Open | Open |
| 36.7 | Retinal capillaries | Closed | Closed | Closed | Closed |
| | Choroidal neoplastic vessels | Closed | Closed | Closed | Closed |
| | Choriocapiliaris | Closed | Closed | Closed | Closed |
| | Choroidal arteries and veins | Closed | Closed | Open | Open |
| 58.8 | Retinal capillaries | Closed | Closed | Closed | Closed |
| | Choroidal neoplastic vessels | Closed | Cldsed | Closed | Closed |
| | Choriocapillaris | Closed | Closed | Closed | Closed |
| | Choroidal arteries and veins | Closed | Closed | Open | Open |

As clearly shown in the above table, the extent of the occlusion of choroidal neoplastic vessels, choriocapillaris, retinal capilaries, choroidal arteries and veins was dependent on the laser irradiation dosage and the interval between the compound administration and laser irradiation. As a result, selective occlusion of the choroidal neoplastic vessels and choriocapillaris was achieved without causing serious damage to the retinal capillaries and choroidal arteries and veins when laser irradiation was performed at 7.4 J/cm$^2$ immediately after administration of the compound or at 22.0 J/cm$^2$ at 2–4 hours after administration.

INDUSTRIES APPLICABILITY

The iminochlorin aspartic acid derivative according to the present invention has a high accumulability to cancerous cells, reactivity to external energy and a cancerous cell destroying effect. Furthermore, it exhibits no toxicity against normal cells because of its quick metabolism in a living body. Accordingly, it is extremely useful as a diagnostic and therapeutic agent for cancers and ophthalmic neovascularization.

What is claimed is:

1. An iminochlorin aspartic acid derivative represented by the following formula (I):

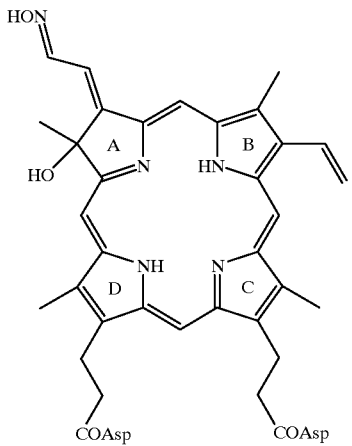

(I)

wherein Asp represents an aspartic acid residue, or a pharmaceutically acceptable salt thereof.

2. A photosensitizer for diagnosis or treatment, comprising the iminochlorin aspartic acid derivative of formula (I) or a pharmaceutically acceptable salt thereof according to claim 1.

3. A method for diagnosing or treating cancer, comprising:
  administering an amount of a photosensitizer according to claim 2 to an animal or human; and
  accumulating the photosensitizer in cancerous tissue.

4. A method for diagnosing or treating cancer according to claim 3, further comprising irradiating the photosensitizer, thereby destroying the cancerous tissue.

5. A method for diagnosing or treating cancer according to claim 4, wherein the cancerous tissue is in an organ selected from the group consisting of lung, muscle, brain, liver, and kidney.

6. A method for diagnosing or treating cancer according to claim 4, wherein said irradiating comprises using a laser having a wavelength of greater than or equal to 670 nm.

7. A method for diagnosing or treating cancer according to claim 4, wherein said irradiating comprises using a laser having a wavelength of less than or equal to 600 nm.

8. A method of diagnosing or treating ophthalmic neovascularization, comprising:
  administering an amount of a photosensitizer according to claim 2 to an animal or human; and
  accumulating the photosensitizer in ophthalmic tissue.

9. A method for diagnosing or treating ophthalmic neovascularization according to claim 8, further comprising irradiating the photosensitizer.

* * * * *